(12) United States Patent
Funamura et al.

(10) Patent No.: US 7,682,340 B2
(45) Date of Patent: Mar. 23, 2010

(54) INDWELLING NEEDLE

(75) Inventors: Shigeaki Funamura, Fukuroi (JP); Yoshihiro Wada, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/013,575

(22) Filed: Jan. 14, 2008

(65) Prior Publication Data
US 2008/0208132 A1 Aug. 28, 2008

(30) Foreign Application Priority Data
Jan. 17, 2007 (JP) ............... 2007-007638

(51) Int. Cl.
*A61M 5/178* (2006.01)
(52) U.S. Cl. ................. 604/167.03; 604/256
(58) Field of Classification Search ............... 604/158, 604/167.03, 246–256
See application file for complete search history.

(56) References Cited

U.S. PATENT DOCUMENTS

| 4,842,591 | A | 6/1989 | Luther |
| 4,917,668 | A | 4/1990 | Haindl |
| 5,156,596 | A | 10/1992 | Balbierz et al. |
| 5,195,980 | A * | 3/1993 | Catlin .............. 604/167.04 |
| 6,544,235 | B2 * | 4/2003 | Motisi et al. ............. 604/249 |
| 2002/0128604 | A1 * | 9/2002 | Nakajima ............. 604/164.01 |
| 2002/0188254 | A1 * | 12/2002 | Steube et al. ............. 604/158 |
| 2004/0127854 | A1 * | 7/2004 | Leinsing et al. ........ 604/167.03 |
| 2005/0043684 | A1 | 2/2005 | Basta et al. |

FOREIGN PATENT DOCUMENTS

| EP | 1240916 A1 | 9/2002 |
| GB | 2427560 A | 1/2007 |
| WO | 03002182 A1 | 1/2003 |

OTHER PUBLICATIONS

Extended European Search Report, Application No. 08100503.5-2310, dated Apr. 17, 2008, 7 pages.

* cited by examiner

*Primary Examiner*—Nicholas D Lucchesi
*Assistant Examiner*—Gerald Landry, II (57) ABSTRACT

An indwelling needle for reducing the deterioration of the valve by the pressure force of the elastic member.

A connector part is provided so as to be moveable within the outer needle body connected to the basal portion of the cannula and provided with the space communicating with the lumen of the cannula therein. Also, within the outer needle body, the valve including the opening and closing aperture through which the tip end side portion of the connector part is liquid tightly penetrated to communicate the lumen of the cannula with the flow path of the connector part as well as the space of the front side portion and the rear side portion of the outer needle body are occluded by closing when the tip end side portion of the connector part is not penetrated therethrough.

5 Claims, 9 Drawing Sheets

INDWELLING NEEDLE

FIELD OF THE INVENTION

The invention relates to an indwelling needle with cannula capable of being indwelled in blood vessels and the like of a human.

BACKGROUND OF THE INVENTION

In conventional practice, a manipulation such that an artificial dialysis is performed or a predetermined medicinal liquid and the like is supplied to, for example, the blood vessels of a patient is carried out with the use of an indwelling needle. The indwelling needle used in such a case includes a cannula for indwelling the needle tip within the blood vessel of the patient and a body portion connected to the basal end portion of the cannula. Then, when the tip end of this cannula is indwelled within the blood vessel, a puncturing needle for the smooth puncturing manipulation of the cannula to the blood vessel is employed. And, when the manipulation described in above is carried out, the puncturing needle is inserted into the indwelling needle to slightly project the tip end portion of the puncturing needle from the tip end portion of the cannula and, in that condition, the cannula together with the puncturing needle is punctured into the blood vessel.

Then, in the condition where the cannula is indwelled in the blood vessel, the puncturing needle is pulled out of the indwelling needle (blood vessel) and the rear end portion of the indwelling needle is connected to a tube member and the like for supplying the escaped blood, the predetermined medicinal liquid or the like to perform the artificial dialysis or supply the medicinal liquid and the like. In such an indwelling needle, there is the indwelling needle in which a valve having an opening and closing aperture is fixed within the body portion and a cylindrical connector part is moveably provided at the rear portion side of the valve within the body part, in which the connector part is pressed forwardly to insert the tip end portion of the connector part into the opening and closing aperture of the valve.

Also, by passing the tip end portion of the connector through the valve, the cannula is communicated with the connector, thereby communicating between the cannula to tube member and the like by connecting the tube member and the like to the rear end portion of the connector part via the rear end portion of the body part (For example, see Japanese Unexamined Patent Publication No. H06-509246. In this indwelling needle (catheter), one end portion of a spring is disposed at the outer peripheral surface of the rear side of the valve (self sealed diaphragm) within the body part (outer cannula hub) and the other end portion of the spring is disposed at a flange like projecting part provided to the rear end portion of the connector (shuttle) to activate the connector rearwardly.

Therefore, when the indwelling needle is indwelled in the blood vessel of the patient, the puncturing needle is inserted into the inside of the connector and then the opening and closing aperture of the valve and, in that condition, the tip end portion thereof is projected from the tip end of the indwelling needle. In this case, the connector part is located at the rear of the valve and the opening and closing aperture of the valve and the puncturing needle are tightly contacted and occluded each other. Then, when the puncturing needle is pulled out of the indwelling needle and the rear end portion of the indwelling needle is connected to the tube member and the like, the connector part is pressed by the tip end portion of the tube member and the like, whereby the tip end portion of the connector part is inserted into the opening and closing aperture of the valve. Thus, the cannula is communicated with the tube member and the like as described in above.

However, in the conventional indwelling needle described in above, since the end portion of the spring is directly contacted with the valve, the elastic force of the spring is applied to the valve all the time which causes the portion of the valve to which the elastic force of the spring is applied become a small streak portion having a small area surface resulting in that the valve may be easily deteriorated and the sealing property thereof may also readily be lowered. Further, there is a fear in this valve that the deterioration by the sterilization or by the elapse of time of a long term storage.

The invention has been made in the light of these problems and the object of the invention is to provide an indwelling needle in which the deterioration of the valve provided therewithin by the pushing pressure of the elastic member can be reduced.

SUMMARY OF THE INVENTION

In one aspect, the present invention is directed to an indwelling needle which comprises: an outer needle including a cannula having a lumen and a cylindrical outer needle body connected to the basal of the cannula and having a space therein for communicating with the lumen of said cannula. A cylindrical connector part moveably provided in the outer needle body along the axial direction of the outer needle body has a flow path therein. An elastic valve having an opening and closing aperture is provided within the outer needle body for communicating the lumen side portion in the space of the outer needle body with the flow path of the connector part by liquid tightly passing through the tip end portion of the connector part and for occluding therebetween in the event of the tip end portion of the connector part is not passed through to shut out between the fore side and the rear side of the space of the outer needle body. A valve holding plate includes an insertion hole provided within the outer needle body along the rear surface of said elastic valve through which the tip end portion of the connector is passed. An elastic member has one end is positioned at the rear surface of said valve holding plate and the other end positioned at a predetermined position of said connector part for activating said connector part toward the rear of said elastic valve.

DESCRIPTION OF FIGURE NOTATIONS 10, 50 each represents the indwelling needle;
10a, 50a each represents the outer needle;
11, 51 each represents the cannula;
11a represent the lumen;
12, 52 each represents the outer needle body;
13, 53 each represents the valve holding plate;
13a, 53a each represents the insertion hole;
14, 54 each represents the valve;
14a, 54a each represents the opening and closing aperture;
15, 55 represents the connector part;
15c, 55c each represents the spring receiving portion;
16 represents the coil spring;
17b represents the space; and
17c, 17d, 18h, 57c, 57d, 58h each represents the step portion.

DETAILED DESCRIPTION OF THE INVENTION

Figure 1:
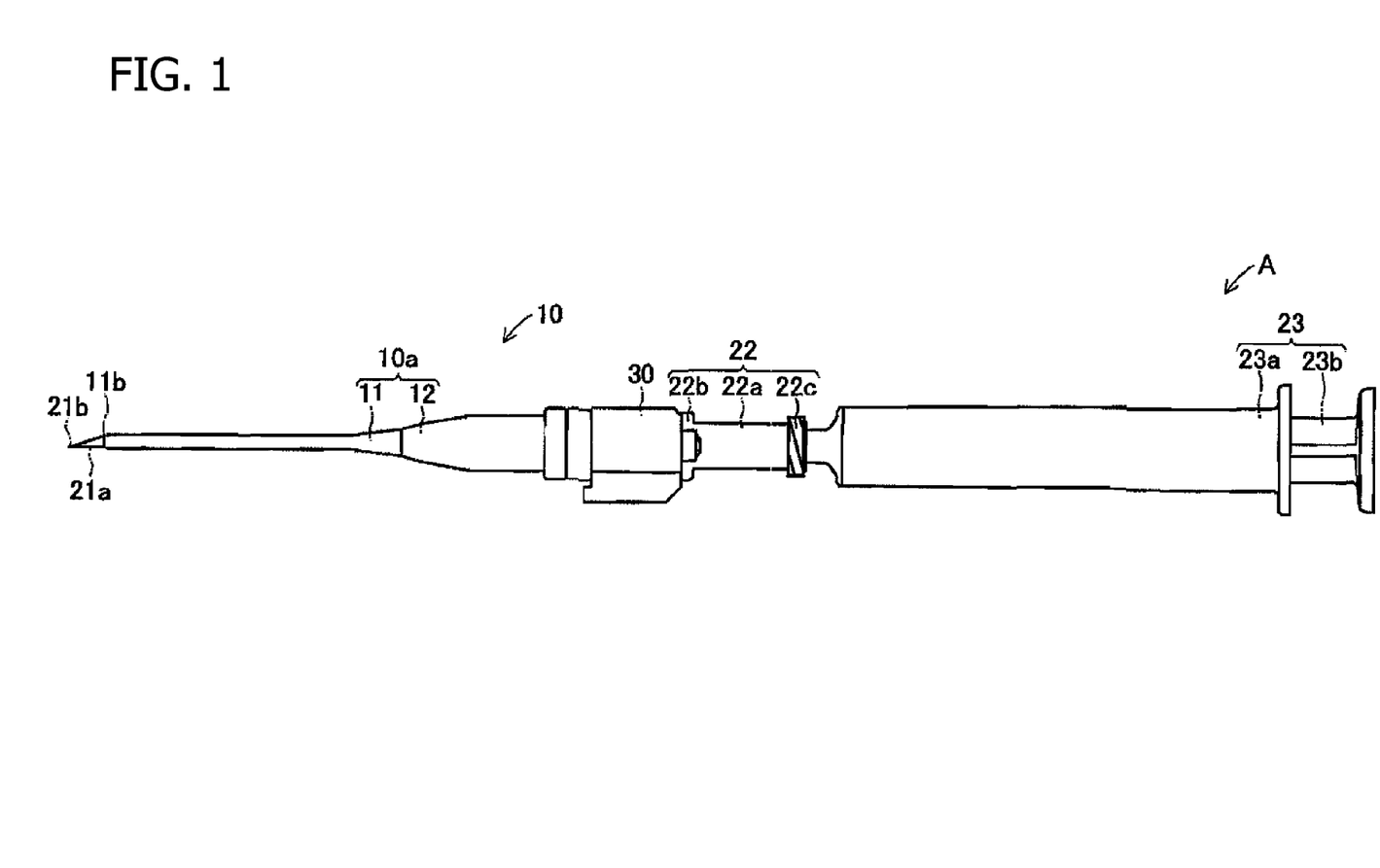
FIG. 1 is a side view illustrating an indwelling needle set having the indwelling needle in accordance with one embodiment of the invention.
Figure 2:
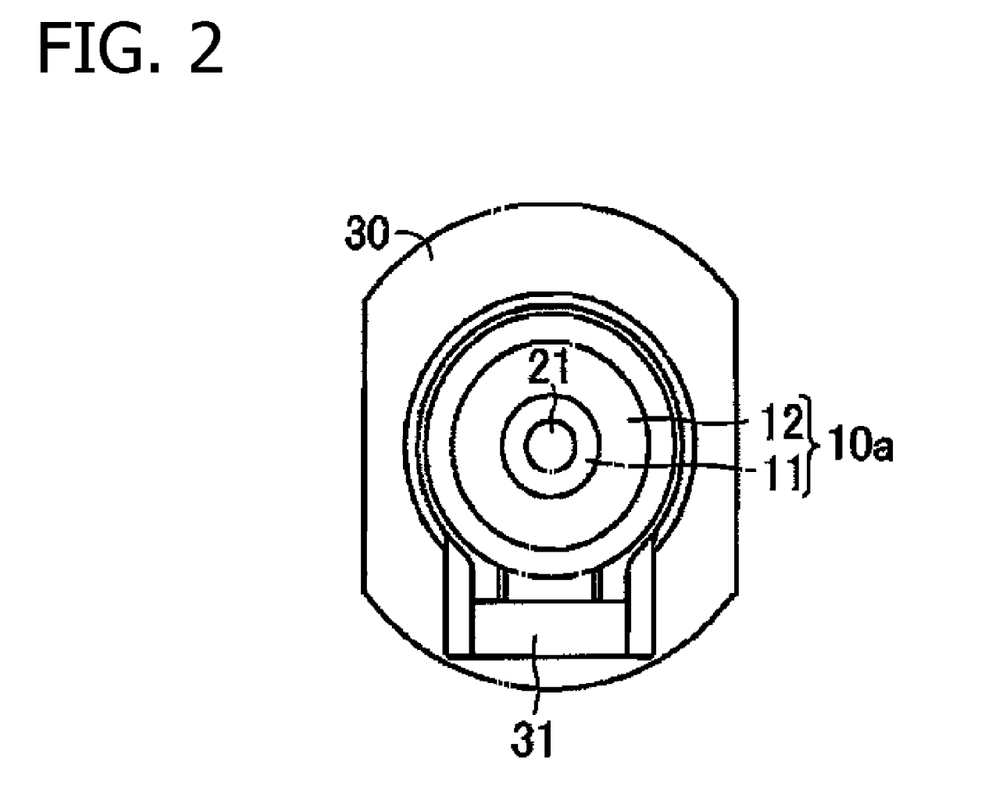
FIG. 2 is a front view illustrating the indwelling needle set.
Figure 3:
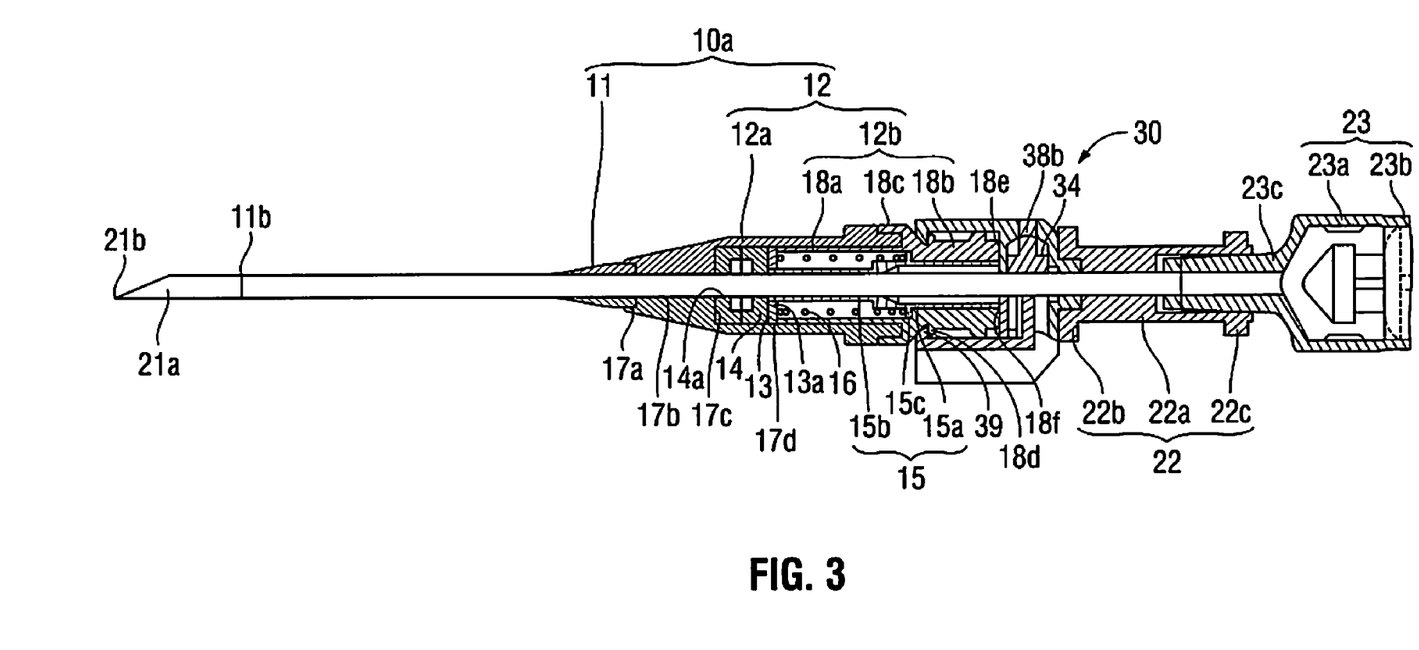
FIG. 3 is a cross sectional view illustrating the indwelling needle set.
Figure 4:
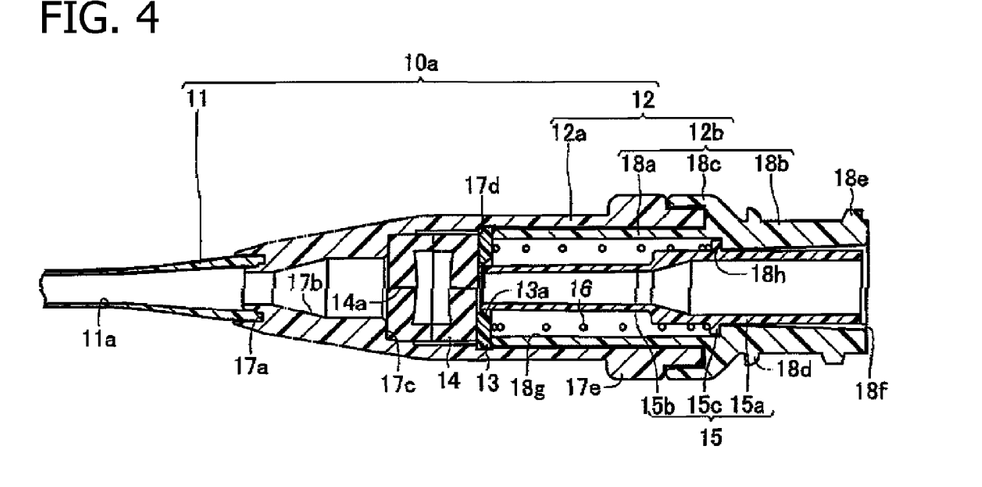
FIG. 4 is a cross sectional view illustrating the indwelling needle.

The indwelling needle in accordance with the invention will now be explained in detail with the reference to the drawings in below. FIGS. 1 to 3 show an indwelling needle set A including an indwelling needle 10 in accordance with the same embodiment. The indwelling needle set A comprises the indwelling needle 10 to be indwelled in a blood vessel of a patient; a puncturing needle 20 (see FIG. 7) having a sharp tip end portion capable of being inserted into the indwelling needle 10 and punctured to the body of the patient; and a needle tip protector 30 and the like. The indwelling needle 10 comprises, as shown in FIG. 4, an outer needle 10a including a narrow tube like cannula 11 and an outer needle body 12 connected to the basal end (the rear end portion located at the right side of the FIG. 4) of the cannula 11; a valve holding plates 13 each provided within the outer needle body 12; a valve 14; a connector part 15; and a coil spring 16.

The cannula 11 includes a lumen 11a forming a flow path perforating from the tip end portion to the rear end portion thereof, the tip end portion 11b is indwelled in the blood vessel of the patient for taking out the blood from the blood vessel or for supplying a medicinal liquid to the blood vessel. Also, the basal end portion of the cannula 11 is formed such that the diameter is gradually increased as closed to the rear portion side. The outer needle body 12 comprises a cylindrical container 12a connected to the basal end of the cannula 12 and a cylindrical connecting portion 12b provided from the inside to the rear side of the cylindrical container 12a.

Furthermore, the front side portion of the cylindrical container 12a is formed into a tapered cylinder in which the size thereof is gradually decreased from the rear side to the front side thereof, to the tip end portion thereof, an annular engagement groove 17a for fixing the basal end portion of the cannula 11 thereto is formed. Also, the rear side portion of the cylindrical container 12a is formed into a cylinder having a generally constant diameter and a space 17b is formed within the cylindrical container 12a such that the front side portion of the space is generally tapered and the rear side of the space is a space having a constant diameter so that the space 17b is complement with the outer profile of the cylindrical container 12a.

Further, to near the boundary portion between the tapered space at the front side and the space at the rear side in the inner peripheral surface of the cylindrical container 12a, a step portion 17c forming a valve controller of the invention is provided, and to the rear end side of the step portion 17c in the inner peripheral surface of the cylindrical container 12a, a step portion 17d having a small difference and forming a pressure controller of the invention is provided so as to keep the predetermined distance from the step portion 17c. These step portions 17c and 17d each formed by making the diameter of the rear side greater than that of the front side of the inner peripheral surface of the cylindrical container 12a. Moreover, to the rear end side portion in the outer peripheral surface of the cylindrical container 12a, a ring like projection 17e being slightly wider (the length in the direction from the front to the rear) is formed along the circumference thereof.

The cylindrical connecting portion 12b comprises an inner cylinder 18a placed within the cylindrical container 12a as contacted with the rear side portion in the inner peripheral surface of the cylindrical container 12a; and a cylindrical part to be engaged 18b rearwardly extended from the rear end portion of the cylindrical container 12a. Further, a ring like projection 18c is formed such that it covers the rear end outer peripheral surface of the cylindrical container 12a from the front end outer peripheral surface to the front of the cylindrical portion to be engaged 18b. The cylindrical connecting portion 12b is connected with the cylindrical container 12a by sandwiching the rear end portion of the cylindrical container 12a by the basal end portion of the lumen 18a and the projection 18c.

When the cylindrical container 12a is connected with the cylindrical connecting portion 12b, the tip end of the projection 18c is contacted with the rear end portion of the projection 17e of the cylindrical container 12a. Furthermore, to the front side portion in the outer peripheral surface of the cylindrical portion to be engaged 18b, a projection to be engaged 18d is formed along the circumference and an external thread 18e is formed to the rear end portion in the outer peripheral surface of the cylindrical portion to be engaged 18b. An inner peripheral surface 18f except for the front end side in the inner peripheral surface of the cylindrical portion to be engaged 18b is formed into a tapered surface such that the diameter thereof at the opening side is gradually decreased as closed to the front side and the diameter of an inner peripheral surface 18g comprising the front end side portion in the inner peripheral surface of the cylindrical portion to be engaged 18b and the inner peripheral surface of the lumen 18a is set so as to be greater than that of the inner peripheral surface 18f. Therefore, a step portion 18h forming the connector controller of the invention is provided between the inner peripheral surface 18g and the inner peripheral surface 18f.

Figure 5:
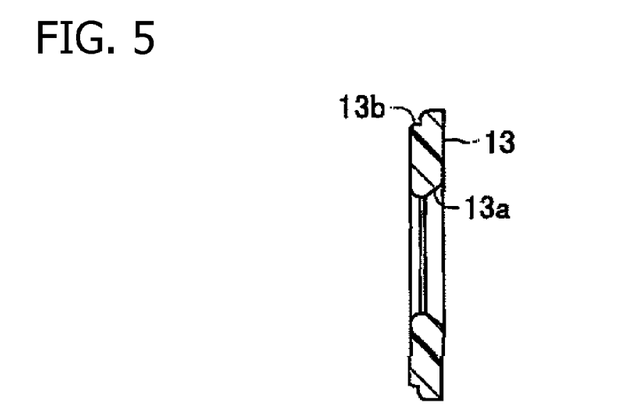
FIG. 5 is a cross sectional view illustrating the valve holding plate.

And, to the portion corresponding to the tip end portion of the lumen 18a in the inner peripheral surface of the cylindrical container 12a, the valve holding plate 13 is provided. Also, within the cylindrical connecting portion 12b, the connector part 15 is provided so as to be moveably in the axial direction of the cylindrical connecting portion 12b. The valve holding plate 13 is formed by a ring like disk and, as shown in FIG. 5, provided with an insertion hole 13a for communicating the front side portion of the space 17b within the cylindrical container 12a with the flow path within the connector part 15 via the valve at the center thereof.

Moreover, the inner peripheral surface of the insertion hole 13a of the valve holding plate 13 comprises two tapered surfaces in which the diameter at the front side portion slightly front side portion relative to the center in the front to back direction is the smallest and the diameter at the rear portion is greater as well as the diameter at the front portion is slightly greater than the smallest diameter at the center side and smaller than the diameter at the rear portion. Also, the valve holding plate 13 is provided with a notch recess 13b the front surface outer periphery side which is capable of being engaged with the step portion 17d provided to the inner peripheral surface of the cylindrical container 12a.

Further, the valve 14 is formed by an elastic member such as an elastic and deformable natural rubber, a synthetic rubber, and isoprene rubber and comprised by a valve being a type of a chamber comprising a pair of circular boxes installed such that openings thereof are opposed to each other. Also, an opening and closing aperture 14a are formed at the portion along to the central axis of the valve 14. Through these opening and closing aperture 14a, the predetermined narrow members can be inserted. When the narrow members are not passed through them, though the valve 14 is maintained in the occluded condition, as shown in FIG. 4, when inner needles 21 of the puncturing needle 20 described in below are inserted therein, as shown in FIG. 3, the narrow members can be contacted with the outer peripheral surface of the inner needles to pass without passing a liquid therethrough.

The valve 14 is set such that the length thereof in the front to back direction is lightly loner than the length between the step portion 17c and the step portion 17d provide on the inner peripheral surface of the cylindrical container 12a in the condition where the valve 14 is not pressed. Also, the valve 14 is positioned in the condition where the outer peripheral portion of the front surface of the valve 14 is contacted with the step portion 17c. Therefore, the valve holding plate 13 is positioned slightly rearward of the step portion 17d when the pressure force is not applied thereto and it pressed forwardly to move forwardly to slightly retract the valve 14. Then, when the notch recess 13b of the valve holding plate is engaged with the step portion 17d of the cylindrical container 12a, the valve holding plate 13 can not be advanced further.

Figure 6:
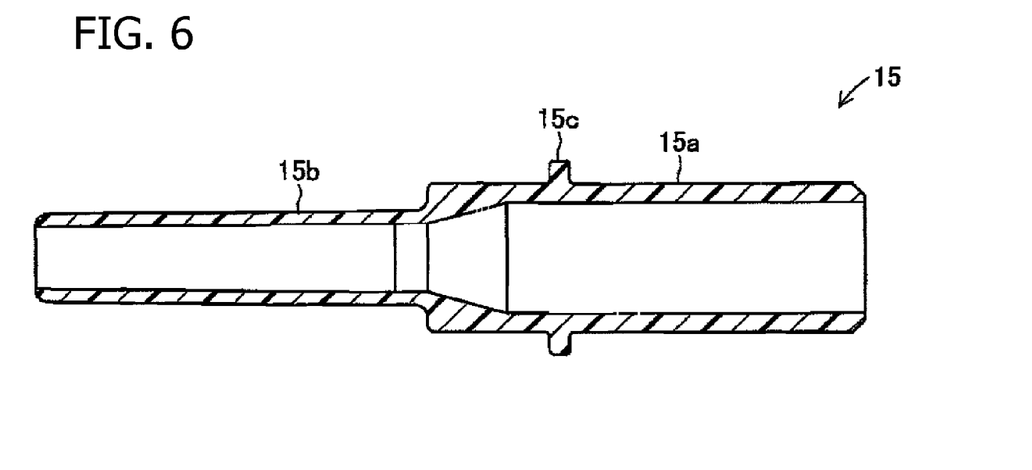
FIG. 6 is a cross sectional view illustrating the connector part.

The connector part 15 comprises two stepped cylinder which length in the axial direction is generally the same as that of the cylindrical connecting portion 12b, in which, as shown in FIG. 6, the rear side is formed by a basal portion 15a having a large diameter and the front side is formed by an insert portion 15b forwardly extended from the front surface of the basal portion 15a and having a small diameter. Then, to the front side portion in the outer peripheral surface of the basal portion 15a, the spring receiving portion 15c comprising a flange like projection is formed along the circumference thereof. Although the spring receiving portion 15c is moveable in the axial direction within the inner peripheral surface 18g of the cylindrical connecting portion 12b, when it is in contact with the step portion 18h, it can not be rearwardly moved further.

And, when the spring receiving portion 15c is in contact with the step portion 18h, the tip end portion of the insert portion 15b is placed within the insertion hole 13a of the valve holding plate 13 and the rear end portion of the basal portion 15a is positioned near the rear end portion of the cylindrical connecting portion 12b. Further, the insert portion 15b is configured such that it can pass through the insertion hole 13a of the valve holding plate 13 and also liquid tightly pass through the opening and closing aperture 14a of the valve 14, and then the insertion portion 15b passes through within the opening and closing aperture 14a of the valve 14, thereby communicating the inside of the connector part 15 with the lumen 11a of the cannula 11 via the space 17b.

And, between the valve holding plate 13 and the spring receiving portion 15c within the lumen 18a, a metallic coil spring 16 forming the elastic member of the invention is provided so as to surround the outer peripheries of the insert portion 15b and the font end portion of the basal portion 15a to rearwardly activate the connector part 15 and forwardly activate the valve holding plate 13. Each of the outer needle 10a of the indwelling needle 10, the valve holding plate 13 and the connector part 15 are formed by a molded resin material.

Figure 7:
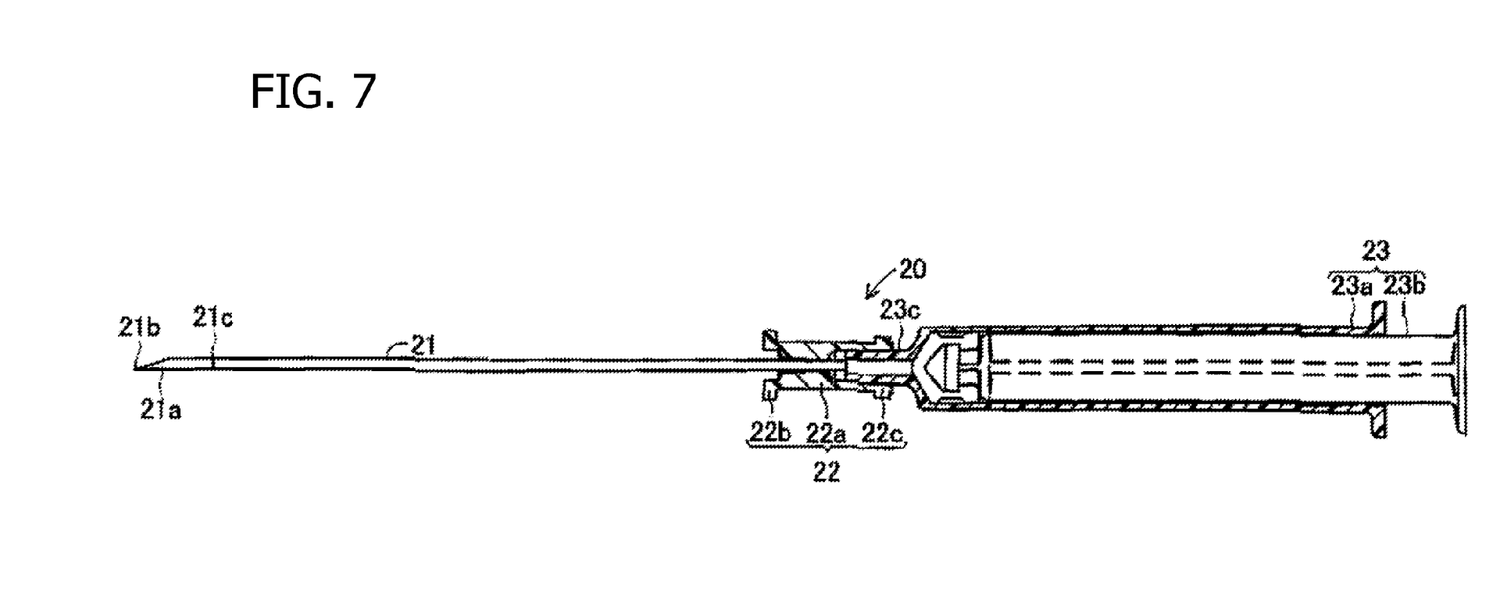
FIG. 7 is a cross sectional view illustrating the condition in which the puncturing needle is attached to the syringe.

The puncturing needle 20 comprises an inner needle 21 made of stainless steel; and a hub 22 fixed to the basal end portion of the inner needle 21 (the rear end portion at the position in the right side in the figures), in which a syringe 23 is connected to the rear portion of the hub 22. The inner needle 21 is comprised by a narrow tube like injection needle having a pronged portion formed such that the tip end portion 21b of the puncturing portion 21a forming the tip end portion is inclined relative to the axial direction. Also, to the rear end portion of the puncturing portion 21a in the inner needle 21, a step portion 21c is formed and the diameter of the puncturing portion 21a is formed so as to be slightly larger than that at the rear end portion including the step portion 21c.

The inner needle 21 is for performing the smooth puncture of the tip end portion 11b of the cannula 11 to the blood vessel of the patient and is penetrated into the indwelling needle 10 from the rear end of the indwelling needle 10 through a needle tip protector 30 explained in below and used in the condition thereof where the puncturing portion 21a is projected from the opening of the tip end portion 11b of the cannula 11 to the exterior. In this case, the puncturing portion 21a of the inner needle 21 will pass through the inside of the needle tip protector 30, connector part 15, the opening and closing aperture 14a of the valve 14, the space 17b of the cylindrical container 12a, and the lumen 11a of the cannula 11 and project from the tip end portion 11b of the cannula 11 to the exterior.

The hub 22 is the portion functioned as a grasping portion for holding the puncturing needle 20 and comprises a resin material fixed to the rear end portion of the inner needle 21 to cover the outer peripheral surface of the basal end portion of the inner needle 21. It is preferred to form this hub 22 by a transparent resin material. Also, the hub 22 comprises a hub body 22a positioned in the center thereof and fixed to the inner needle 21, a flange like container 22b formed at the front portion of the hub body 22a while being apart from the periphery of the inner needle 21 by the predetermined distance, and a cylindrical female lure part 22c formed at the rear portion of the hub body 22a and including a recess opened rearwardly.

Moreover, the female lure part 22d is provided with the syringe 23 attached thereto. The syringe 23 comprises a cylinder portion 23a and a piston portion 23b, in which a male lure part 23c formed to the tip end portion of the cylinder portion 23a is inserted into the female lure part 22c to connect the syringe 23 with the puncturing needle 20. Also, the hub 22 may be used with a ventilation plug including an air filter capped thereto, whereby the blood becomes to backflow as the needle tip of the inner needle 21 reaches to the blood vessel so that the reach of the needle tip of the inner needle 21 can readily be confirmed.

Figure 8:
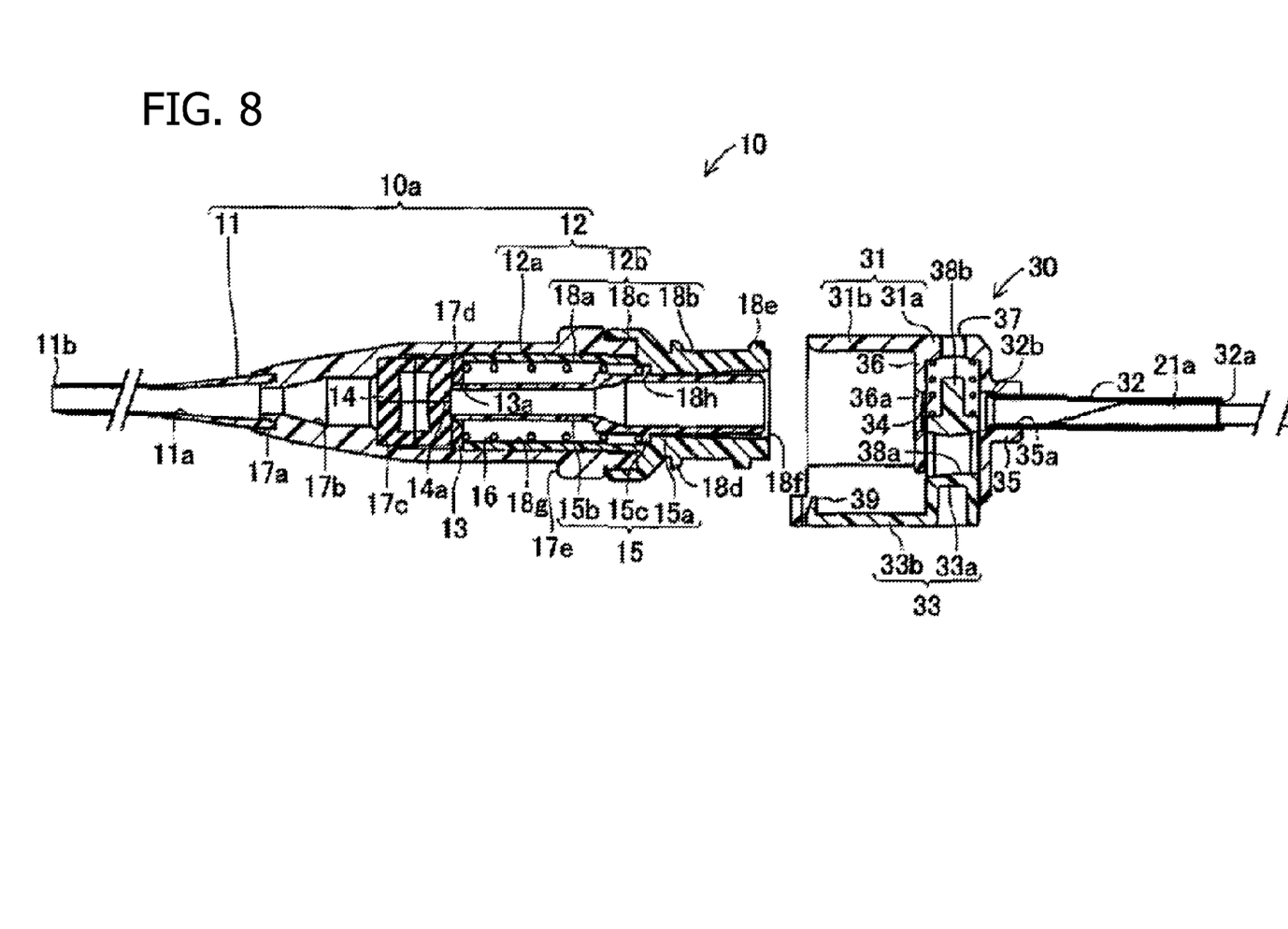
FIG. 8 is a cross sectional view illustrating the condition in which the needle tip protector and the puncturing needle are taken out of the indwelling needle.

Furthermore, to the outer periphery of the cylindrical portion to be engaged 18b of the outer needle body 12, as shown in FIGS. 1, 3 and 8, the needle tip protector 30 is mounted and the inner needle 21 of the puncturing needle 20 passes through this needle tip protector 30 to extend to the tip end side of the cannula 11. This needle top protector 30 comprises a protector body 31 in which the cylindrical portion to be engaged 18b can be received from the front end opening, a needle tip protecting cylinder 32 attached to the protector body 31 while being forwardly and backwardly moveable from the rear portion of the protector body 31 to the exterior, an engagement member 33 attached while being upwardly and downwardly moveable within the protector body 31, and a coil spring 34.

The protector body 31 comprises a generally box shaped case member provided with openings at the front surface and the bottom surface and an engagement cylinder 35 outwardly and backwardly extended at the rear wall surface, in which the upper side portion thereof is formed into a generally cylindrical shape along with the profile of the cylindrical portion to be engaged 18b and the lower side portion is formed by a pair of wall portions disposed in a generally parallel with a certain distance. Moreover, within the engagement cylinder 35, a engagement hold 35a having a diameter at the front side portion (the portion located within the protector body 31) slightly greater than that at the rear side portion and a difference between the front portion and the rear portion is provided.

Also, to the slightly rear portion from the center in the front to back direction within the protector body 31, a partition 36 for partitioning the front and the rear portions in the upper side portion of the protector body 31, the rear portion from the partition 36 in the protector body 31 is formed into an engagement member receiving portion 31a and the front portion from the partition 35 is formed into a cover 31b covering the cylindrical portion to be engaged 18b. Then, to the portion opposed to the engagement hole 35a of the engagement cylinder 35 in the partition 36, an insertion hole 36a set so as to have a diameter generally same as the larger diameter of the engagement hole 35a is formed on the same axis of the engagement hole 35a. Further, to the ceiling of the engagement member receiving portion 31a, a circular projection hole 37 is formed.

The needle tip protecting cylinder 32 is formed such that the length in the axial direction is slightly longer than the length in the front to back direction of the protector body 31, in which the rear end opening is formed into a narrow opening 32a through which the rear end opening, the rear side portion more rear than the puncturing portion 21a in the inner needle 21 of the puncturing needle 20 can be passed but the puncturing portion 21a can not be passed; and the front end opening is formed into a larger opening 32b through which the puncturing portion 21a. Moreover, the larger opening 32b of the needle tip protecting cylinder 32 is formed to a size such that the insertion hole 35a of the protector body 31 and the larger portion of the front portion of the engagement hole 35a can be passed through while the narrow portion of the rear portion of the engagement hole 35a can not be passed through.

Accordingly, into the needle tip protecting cylinder 32, the inner needle 21 is inserted while the puncturing portion 21a is projected from the rear portion thereof, in that condition, the needle tip protecting cylinder 32 can be forwardly and backwardly moved from the rear portion to the exterior of the protector body 31 through the insertion hole 36a and the engagement hole 35a. That is to say, when the needle tip protecting cylinder 32 is contained within the protector body 31, the needle tip protecting cylinder 32 is in the condition where the narrow opening 32a is disposed within the engagement hole 35a by penetrating the insertion hole 36a, as well as, when the needle tip protecting cylinder 32 is projected from the rear portion of the protector body 31, the needle tip protecting cylinder 32 allows the larger opening 32b to engage with the difference of the engagement hole 35a, thereby preventing it from being pulled out of the protector body 31.

The engagement member 33 is provide in the condition where it is upwardly and downwardly moveable within the protector body 31 and comprises an engagement body 33a and an engagement piece 33b. The engagement body 33a is disposed within the engagement receiving portion 31a and the engagement piece 33b is disposed at the lower side portion of the cover 31b. the engagement body 33a is formed to be longitudinal and a frame including a polygonal such as rectangular and the like of a circular engagement hole 38a through which the needle tip protecting cylinder 32 can be passed is provided at the center portion.

Furthermore, to the upper portion of the frame body of the engagement body 33a, a cylindrical engagement portion 38b capable of being engaged with the ceiling of the engagement member receiving portion 31a by forwardly and backwardly moving relative to the projecting hole 37 of the protecting body 31 is formed. Moreover, the cross sectional shape of the lower side portion of the engagement boy 33a is formed into a U shape downwardly opened, from the lower front end, the engagement piece 33b is extended toward the front. Also, at the front end upper surface of the engagement piece 33b, an engagement claw 39 upwardly projected is formed. The engagement claw 39 can be engaged with the projecting portion to be engaged 18d of the cylindrical portion to be engaged 18b.

Moreover, between the upper surface of the frame portion of the engagement member 33 and the ceiling of the engagement receiving portion 31a of the protector body 31, the stainless steel coil spring 34 is mounted so as to surround the engagement portion 38b. This coil spring 34 is set to have a diameter greater than that of the projecting hole 37, thereby preventing it from being projected from the projecting howl 37. Therefore, when the engagement member 33 is upwardly moved, the engagement portion 38b is positioned within the projecting hole 37 and the coil spring 34 is retracted against the upward movement force of the engagement member 33. Also, when the force retaining the engagement member 33 in the upper is released, the coil spring 34 is extended to activate the engagement member 33 toward the lower side within the protector body 31.

The needle tip protector 30 configured in this way is installed to the indwelling needle 10 with the cylindrical portion to be engaged 18b is contained within the cover portion 31b. Also, the needle tip protector 30 is installed to the puncturing needle 20 by positioning the needle tip protecting cylinder 32 through which the inner needle 21 is passed within the insertion hole 36a and the engagement hole 35a. At that time, by passing the needle tip protecting cylinder 32 through the engagement hole 38a of the engagement member 33, the engagement member 33 is maintained to be pushed up to the upper to allow the engagement portion 38b to enter the projecting hole 37.

Also, at that time, the engagement claw 39 of the engagement member 33 is engaged with the projecting portion to be engaged 18d of the cylindrical potion to be engaged 18b. By this engagement of the engagement claw 39 with the projecting portion to be engaged 18d, the needle tip protector 30 is maintained to be fixed to the outer needle body 12. Further, by pushing the puncturing needle 20 against the needle tip protecting cylinder 32, the engagement cylindrical portion 35 of the protector body 31 is inserted into the container 22b of the hub 22. According to this, as shown in FIGS. 1 and 3, the puncturing portion 21a of the inner needle 21 is projected from the tip end portion 11b of the cannula 11. Also, in this case, the coil spring 16 is extended to allow the connector part 15 to position at the rear end side of the outer needle body 12 and the front side portion of the needle tip protecting cylinder 32 enters into the basal portion 15a of the connector part 15. In this way, the indwelling needle 10, the puncturing needle 20 and the needle tip protector 30 are assembled, thereby providing the indwelling needle set A as shown in FIGS. 1 to 3.

In this configuration, by the use of the indwelling needle set A, when the blood is taken from the blood vessel of the patient, for example, firstly, the tip end portion 11b of the cannula 11 of the indwelling set A together with the puncturing portion 21a of the inner needle 21 is punctured in an arm of the patient to the blood vessel. Then, the piston portion 23b of the syringe 23 is gradually pulled out of the cylinder portion 23a. According to this, the blood in the blood vessel enters into the inner needle 21 and, then, the side portion of the hub body 22a of the hub 22 or the cylinder portion 23a. As a result, the color of the hub 22 or the cylinder portion 23a is turned red, thereby determining the reach of the puncturing portion 21a of the inner needle 21.

Next, the puncturing needle 20 together with the syringe 23 is pulled to the rear portion of the indwelling needle 10 while the tip end portion 11b of the indwelling needle 10 is indwelled within the blood vessel of the patient. According to this, the inner needle 21 is backwardly moved from the indwelling needle 10 and the needle tip protector 30 as slidingly contacted with the peripheral surface of the opening and closing aperture 14a of the valve 14. In this case, the inner needle 21 passes through the opening and closing aperture 14a of the valve 14 while the inner needle 21 is liquid tightly contacted with the inner peripheral surface of the opening and closing aperture 14a, thereby preventing the blood from leaking from the opening and closing aperture 14a to the exterior. Further, after the inner needle 21 is took out, the opening and closing aperture 14a becomes to be occluded, thereby preventing the blood from flowing the rear end portion of the outer needle body 12.

Moreover, when the puncturing needle 20 is pulled toward the rear portion of the indwelling needle 10 and the puncturing portion 21a of the inner needle 21 is engaged with the narrow opening 32a of the needle tip protecting cylinder 32, the needle tip protecting cylinder 32 together with the puncturing needle 20 is also moved rearwardly. Then, when the larger opening 32b is passed through the insertion hole 36a of the partition 36 and the engagement hole 38a of the engagement member 33 by the movement of the needle tip protecting cylinder 32, the engagement member 33 is downwardly moved by the restoring force of the coil spring 34 to release the engagement between the engagement claw 39 and the projecting portion to be engaged 18d. As a result, the needle tip protector 30 becomes to be moveable to release together with the inner needle 21 from the indwelling needle 10 shown in FIG. 8.

Figure 9:
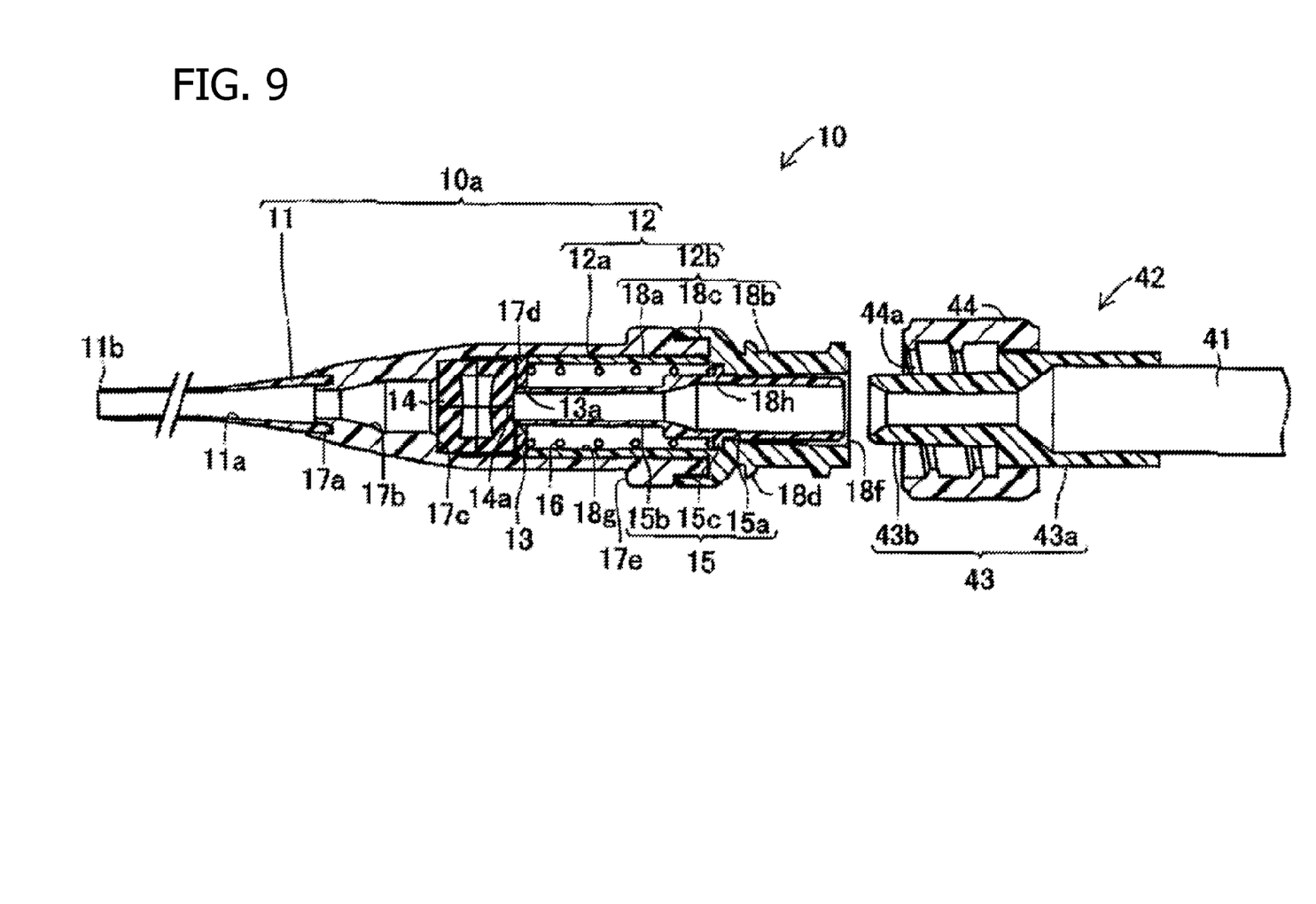
FIG. 9 is a cross sectional view illustrating the condition in which the tube member is being connected to the indwelling needle.

Next, the case in which the medicinal liquid and the like is supplied by connecting a tube member 41 (see FIGS. 9 and 10) to the outer needle body 12 of the indwelling needle 10 indwelled in the blood vessel of the patient will be explained in below. In this case, a connector 42 provided to the tube member 41 at the tip end thereof is connected to the cylindrical portion to be engaged 18b of the outer needle body 12 and the basal portion 15a of the connector part 15. This connector 42 comprises a connector body 43 fixed to the tip end of the tube member 41 and a cap like cylindrical connecting portion 44 attached so as to be rotatable about the axis to the outer periphery of the connector body 43.

Figure 10:
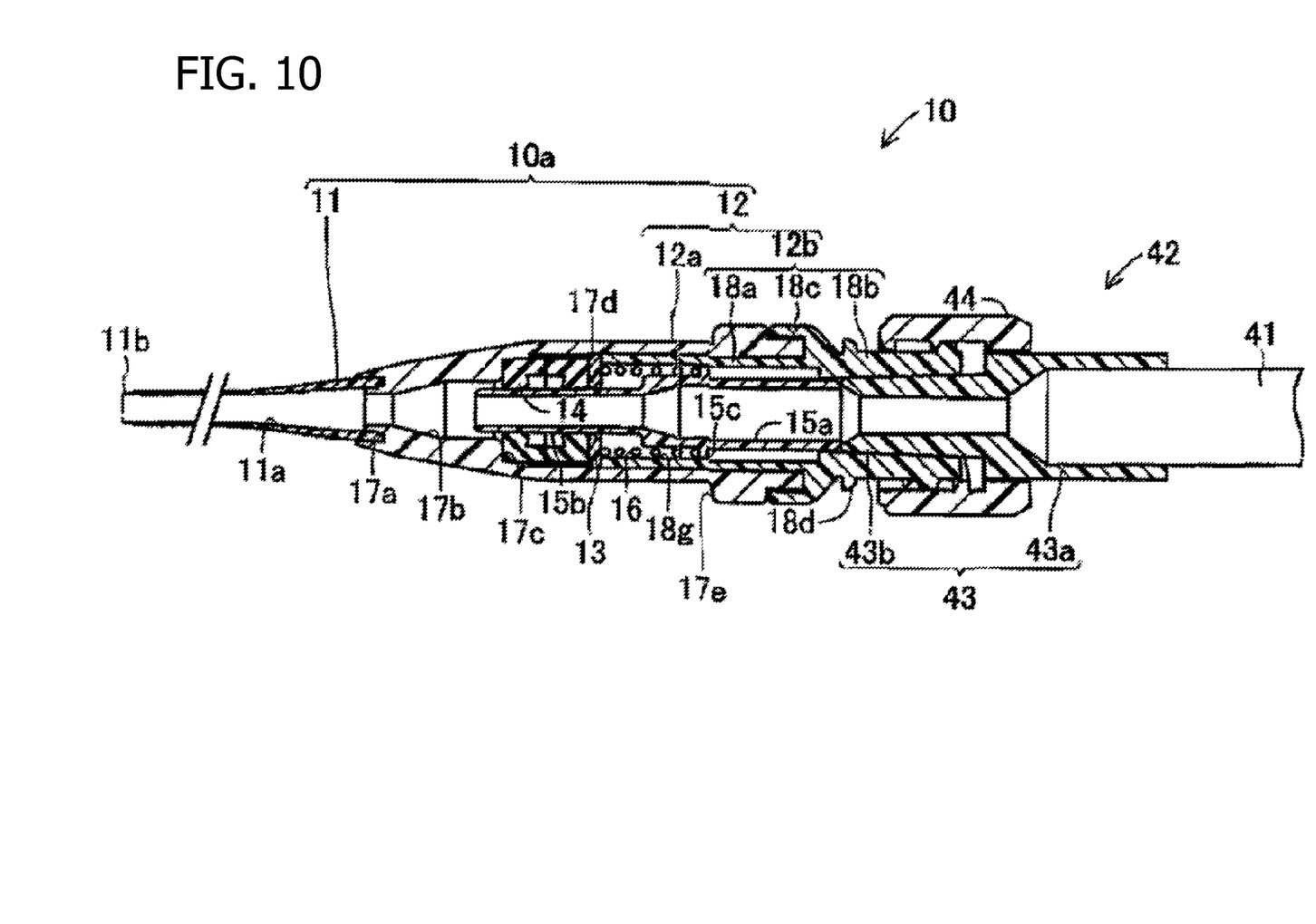
FIG. 10 is a cross sectional view illustrating the condition in which the tube member has been connected to the indwelling needle.

The connector body 43 comprises a fixing portion 43a fixed to the tip end outer periphery of the tube member 41, and a tapered male lure part 43b that can be inserted from the rear end portion into the inside of the cylindrical portion to be engaged 18b and tightly contacted with the inner peripheral surface 18f. Also, to the inner peripheral surface of the cylindrical connecting portion 44, an internal thread 44a that can be engaged with the external thread 18e of the outer needle body 12 is formed. This connecting portion 42 is connected to the indwelling needle 10 to provide the condition as shown in FIG. 10 by inserting the male lure part 43b into the cylindrical portion to be engaged 18b to helically engage the internal thread 44a with the external thread 18e.

When the connecting portion 42 is connected to the indwelling needle 10, the male lure part 43b forwardly pushes and moves the connector part 15 against the elastic force of the coil spring 16. According to this, the insertion portion 15b of the tip end side of the connector part 15 penetrates the opening and closing aperture 14a of the valve 14 to communicate with the lumen 11a of the cannula 11 via the space 17b of the cylindrical container 12a. At that time, by the movement of the connector part 15, the coil spring 16 is retracted and presses the valve holding plate 13 forwardly. Therefore, the valve 14 is pressed to contact with the step portion 17d of the valve holing plate 13 to maintain the sealing ability of the valve 14 in good condition. In this way, with the connecting portion 42 connected with the indwelling needle 10, a medicinal liquid and the like supply device (not shown) connected to the basal end portion of the tube member 41 is activated to supply the medicinal liquid and the like to the blood vessel.

In this way, in the indwelling needle 10 according to the embodiment of the invention, the valve holding plate 13 is provided to the rear surface of the valve 14 and the coil spring 16 is positioned through this valve holding plate 13. Thus, it can be eliminated that the rear surface of the valve 14 is directly and locally pressed at the end portion of the coil spring. As a result, the deterioration of the valve 14 by the local pressure can be reduced and the excellent sealing ability thereof can be maintained. Further, the step portion 17c for preventing the valve 14 from moving forwardly is provided at the portion where the front peripheral edge portion of the valve 14 is located in the inner peripheral surface of the cylindrical container 12a as well as the step portion 17d for controlling the force pushing the valve 14 of the valve holding plate 13 with the activating force of the coil spring 16 is provided at the portion opposed to the front surface peripheral edge portion of the valve holding plate 13 in the inner peripheral surface of the cylindrical container 12a. Accordingly, it can be prevented that the pressure force more than required is applied to the valve 14, thereby securely reducing the deterioration of the valve 14 by the pressure force of the coil spring 16.

Moreover, in the indwelling needle 10 according to the embodiment of the invention, the spring receiving portion 15c is provided at the front side portion in the outer peripheral surface of the basal portion 15a of the connector 15 as well as the step portion 18h for preventing the connector part 15 from rearwardly moving is provided at the portion where the rear end portion of the spring receiving portion 15c is located in the cylindrical connecting portion 12b of the outer needle body 12. Also, when the spring receiving portion 15c is contacted with the step portion 18h, the tip end portion of the connector part 15 is located within the insertion hole 13a of the valve holding plate 13 and when the connector part 15 is forwardly moved against the elasticity of the coil spring 16, the tip end portion of the connector part 15 is penetrated into the opening and closing aperture 14a of the valve 14 and projected from the front surface side of the valve 14.

According to this, when the connector part 15 is moved forwardly, even though the direction in which the connector part 15 is pressed is deviated from the axial direction of the connector part 15, the connector part 15 is advanced in a straight line with the insertion hole 13a as a guide and the tip end portion thereof enters the opening and closing aperture 14a of the valve 14. Further, since the valve holding plate 13 is formed into a tapered shape having the inner peripheral surface of the insertion hole 13a in which the diameter at the rear portion side is larger than that at the front portion side, the tip end portion of the connector part 15 certainly enters into the insertion hole 13a at the center with the inner peripheral surface of the insertion hold 13a as a guide when the connector part 15 is moved forwardly. Thus, the connector part 15 is forced to be a straight and advanced, whereby the tip end portion thereof penetrates the opening and closing aperture 14a of the valve 14.

Figure 11:
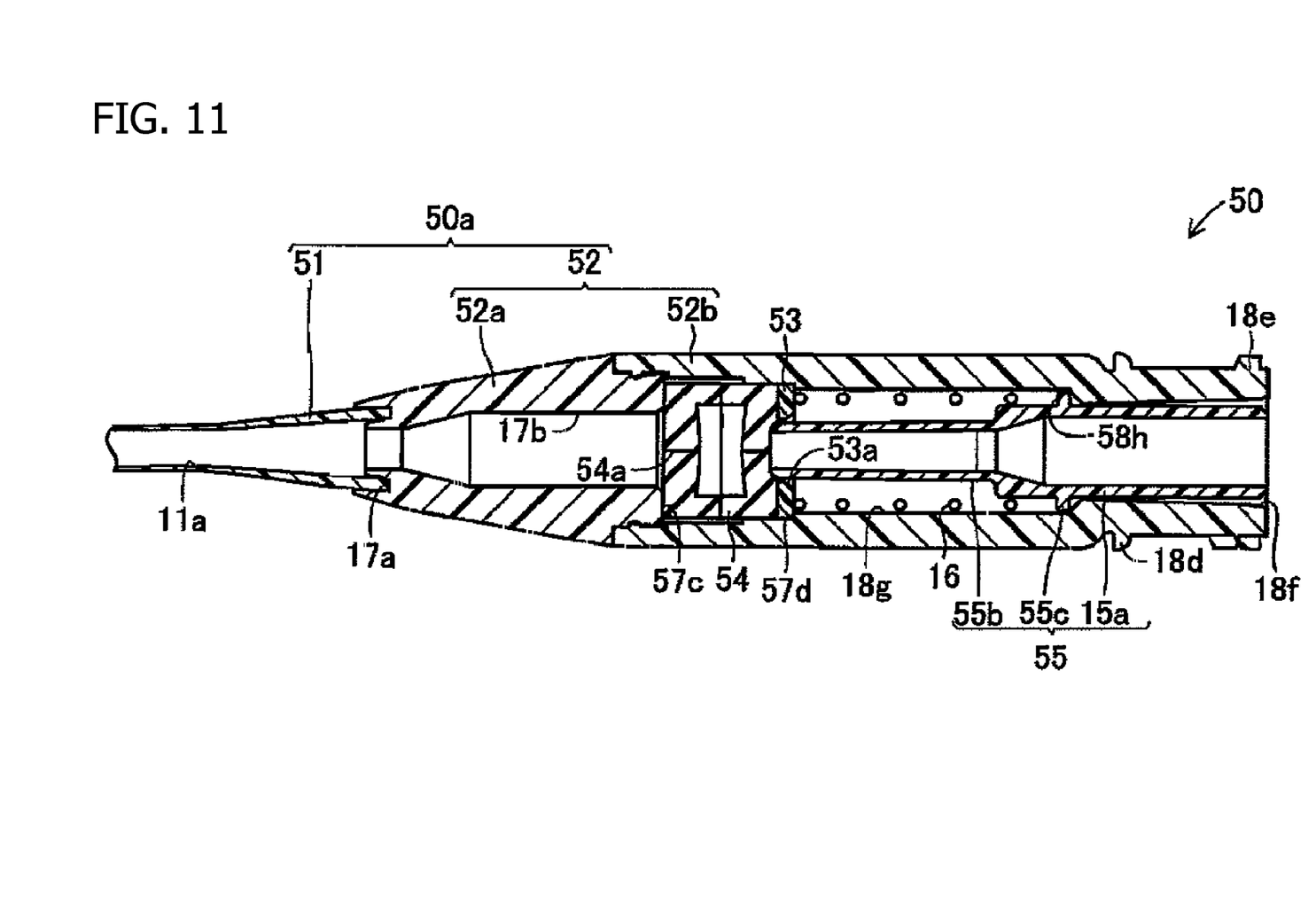
FIG. 11 is a cross sectional view illustrating the indwelling needle in accordance with another embodiment of the invention.

Moreover, FIG. 11 shows an indwelling needle 50 of another embodiment in accordance with the invention. In this indwelling needle 50, an outer needle body 52 of an outer needle 50a comprises a cylinder portion 52a connecting to the basal end portion of a cannula 51, and a cylindrical receiving and connecting portion 52b rearwardly extended from the rear end portion of the cylinder 52a. Then, the cylinder 52a is formed into a tapered shape having the rear portion side is gradually tapered as closed to the front portion side. Further, the front side portion and the center side portion of the cylindrical receiving and connecting portion 52b is formed into a cylinder having a generally constant diameter and a step portion 57c forming a valve controller of the invention is formed at the boundary between the cylinder portion 52a and the cylindrical receiving and connecting portion 52b in the inner peripheral surface of the outer needle body 52.

Also, at the rear portion side of the step portion 57c in the inner peripheral surface of the cylindrical receiving and connecting portion 52b, a step portion 57d for a backward movement controller of the invention having a small difference is formed with the predetermined distance from the step portion 57c. Between the step portion 57c and the step portion 57d in this cylindrical receiving and connecting portion 52b, a valve 54 same as the valve 14 and a valve holding plate 53 same as the valve holding plate 13 are disposed at the front and the rear, respectively, and the valve 54 is prevented from forwardly moving by the step portion 57c as well as the valve holding plate 53 is prevented from rearwardly moving by the step portion 57d. Further, at the portion slightly rear from the center in the inner peripheral surface of the cylindrical receiving and connecting portion 52b, a step portion 58h having an inclined surface forming the connector controller of the invention is provided.

Moreover, when a spring receiver 55c formed to the connector part 55 is contacted with the step portion 58h, the tip end portion of the insertion portion 55b of the connector part 55 penetrates the insertion hole 53a of the valve holding plate 53 to enter the inside of the rear end side portion of the opening and closing aperture 54a of the valve 54. Also, to the cylindrical receiving and connecting portion 52b, the projection 17e or the projection 18c provided to the outer needle body 12 described in above are not provided. The other components other than the indwelling needle 50 are the same as those of the indwelling needle 10 described in above. Thus, the explanation thereof is omitted by indicating the same components with the same referential numbers. The same effects obtainable by the indwelling needle 10 described in above can be achieved.

Moreover, the indwelling needle in accordance with the invention is not intended to limited to the embodiments described in above, various modifications thereof may be made. For example, though the valve holding plates 13 and 53 are formed by a ring like disc having insertion holes 13a and 53a, this valve holding plates 13 and 53 may be formed to have another configuration. For example, the valve holding plates 13 and 53 may be provided with a cylindrical guide portion extended rearwardly from the peripheral edge of the insertion holes 13a and 53a thereof. According to this, the tip end side portion of the insertion portions 15b, 55b of the connector part 15, 55 can be positioned in the inside of the insertion holes 13a, 53a or the guide portion all the time, whereby the front to back movement of the connector part 15, 55 can be smooth.

Further, the valve holding plates 13 and 53 may be formed by a polygon such as a rectangular plate or a triangular plate having an insertion hole or another shaped plate, not a ring like disc. Moreover, the embodiment described in above, though the valve holding plates 13, 53 and the one end of the coil spring 16 are just contacted with the other end of the coil spring 16 one another and the spring receiving portions 15c, 55c, these portions may be fixed one another. Also, in the indwelling needle 10 as described in above, when the connector part 15 is forwardly moved, the valve holding plate 13 can be moved by the pressure force of the coil spring 16, however, the valve holding plate 13 may be contacted with the step portion 17d all the time to push the valve 14 by the constant pressure force.

Further, in the embodiment described in above, thought the metallic coil spring 16 is employed as the elastic member activating the connector part 15 rearwardly, for this elastic member, a coil spring made of resin, a rubber bellows, a coupler bar (that similar to the elastic member provided below a key of a keyboard) and the like other than the metallic coil spring 16 may be employed. Also, various modifications may be applied to the other components of the indwelling needle in accordance with the invention within the scope of the invention.

In the indwelling needle of the invention configured as described in above, the elastic member for activating the connector part toward the rear side of the outer needle body is provided not in the condition where the elastic member is directly contacted with the elastic valve but in the condition where the valve holding plate is provided at the rear surface of the elastic valve through which the elastic member is provided. Therefore, it is eliminated that the rear surface of the elastic valve is directly and locally pressed at the end portion of the elastic member. As a result, the fear that the elastic valve is deteriorated can be reduced, thereby maintaining the good sealing ability thereof. In this case, the valve holding plate and one end of the elastic member as well as the other end of the elastic member and the predetermined portion of the connector part, respectively, may only be contacted with or fixed to each other.

Further, other configurational characteristic of the indwelling needle in accordance with one embodiment of the invention is that the indwelling needle further comprises: a valve controller for preventing the forward movement of the elastic valve provided at the portion where the front periphery of the elastic valve is located in the outer needle body; and a pressure controller for controlling the pressure force of the valve holding plate against the elastic valve by the activating force of the elastic member provided at the portion opposite to the front periphery of the valve holding plate in the outer needle body.

According to this, the elastic member can not press the elastic valve with a certain force or above when the elastic member is pressed by the movement of the connector part to press the elastic valve through the valve holding plate with the elastic force thereof. Thus, it can be prevented to apply the pressure force more than required to the elastic valve, thereby securely reducing the deterioration of the elastic valve due to the pressure force of the elastic member. In this case, the valve holding plate may be in the stationary while being contacted with the pressure controller or may be moveable within the predetermined range. The control of the pressure force as the valve holding plate is moveable within the predetermined range is carried out by controlling the range where the valve holding plate is forwardly moveable. That is to say, the force over the pressure force as the elastic valve is pressed by the valve holding plate with the proper force to exhibit a good sealing ability is not applied to the elastic valve.

And yet another configurational characteristic of one embodiment of the indwelling needle of the invention is that the indwelling needle further comprises: a valve controller for preventing the forward movement of the elastic valve provided at the portion where the front periphery of the elastic valve is located in the outer needle body; and a backward movement controller for controlling the backward movement of the valve holding plate provided at the portion opposite to the rear periphery of the valve holding plate in the outer needle body. According to this, it can be prevented that the pressure force pressing the elastic valve is not reduced to lower than the predetermined magnitude, thereby maintaining the sealing ability of the elastic valve with or without the pressure force of the elastic member.

Further, another configurational characteristic of the indwelling needle in accordance with one embodiment of the invention is that: in which the elastic member is formed by a spring and the predetermined portion of the connector part is formed by a spring receiving portion projected from the outer peripheral surface of the connector part, the indwelling needle include a connector controller for controlling the backward movement of the connector part provided at the portion opposite to the rear end portion of the spring receiving portion in the outer needle body, whereby the tip end portion of the connector part is located within the insertion hole of the valve holding plate or near thereof as the spring receiving portion is contacted with the connector controller and the tip end portion of the connector part is passed through the opening and closing aperture of the elastic valve to project the rear surface side of the elastic valve when the connector part is forwardly moved against the elasticity of the spring.

In the indwelling needle configured in this way, the tip end portion of the spring can be positioned at the predetermined portion of the connector by such a simple structure. Further, according to this, the connector part can be moved in a proper condition. That is to say, as long as the tip end portion of the connector part is located at the position where the tip end portion is within or passed through the insertion hole of the valve holding plate, the connector part is advanced in a straight line and the tip end portion thereof passes through the opening and closing aperture of the elastic valve when the connector part is forwardly moved against the elasticity of the spring even though the direction in which the connector part is pressed is deviated from the axial direction of the connector part because the insertion hole acts as a guide. Moreover, when the connector part is backwardly moved, even though the tip end portion thereof is not at the position where the tip end portion is within or passed through the insertion hole of the valve holding plate, the tip end portion will pass through the opening and closing aperture of the elastic valve as the connector part is forwardly moved because the position of the tip end portion is near the insertion hole.

Also, another configurational characteristic of the indwelling needle in accordance with one embodiment of the invention is that the inner peripheral surface of the insertion hole of the valve holding plate is formed into a tapered shape such that the diameter at the rear side is greater than that at the front side. According to this, when the connector part is forwardly moved, the tip end portion of the connector part is securely inserted in the insertion hole about the center thereof because the inner peripheral surface of the insertion hole act as a guide, whereby the connector part is forced into the position relative to the axial direction and advanced to pass the tip end portion thereof through the opening and closing aperture of the elastic valve. Accordingly, even though the connector part is activated to backwardly move by the elastic member and the tip end portion of the connector part is positioned at the rearward than the valve holding plate, the tip end portion of the connector part can readily be inserted into the insertion hold when the connector part is forwardly moved. Further, the benefit of the easy positioning of the valve holding plate relative to the connector part can be provided.

What is claimed is:

1. An indwelling needle according to the invention, wherein said indwelling needle comprises:
   an outer needle including a cannula having a lumen and a cylindrical outer needle body connected to the basal of the cannula and having a space therein for communicating with the lumen of said cannula;
   a cylindrical connector part moveably provided in the outer needle body along the axial direction of the outer needle body and having a flow path therein;
   an elastic valve defining a chamber, the valve including a pair of substantially symmetrical circular portions, each having an open end and a substantially closed end defining a closing aperture, wherein the valve is provided within the outer needle body with the open ends facing one another, for communicating the lumen side portion in the space of the outer needle body with the flow path of the connector part by liquid tightly passing through the tip end portion of the connector part and for occluding therebetween in the event of the tip end portion of the connector part is not passed through to shut out between the fore side and the rear side of the space of the outer needle body;
   a valve holding plate including an insertion hole provided within the outer needle body along the rear surface of said elastic valve through which the tip end portion of the connector is passed; and
   an elastic member in which one end is positioned at the rear surface of said valve holding plate and the other end is positioned at a predetermined position of said connector part for activating said connector part toward the rear of said elastic valve;
   wherein the valve holding plate is coupled between the elastic valve and the elastic member to prevent the elastic member from applying a force directly onto the elastic valve.

2. The indwelling needle according to claim 1, wherein the indwelling needle further comprises:
   a valve controller for preventing the forward movement of said elastic valve provided at the portion where the front periphery of said elastic valve is located in the outer needle body; and
   a pressure controller for controlling the pressure force of said valve holding plate against said elastic valve by the activating force of said elastic member provided at the portion opposite to the front periphery of said valve holding plate in said outer needle body.

3. The indwelling needle according to claim 1, wherein the indwelling needle further comprises:

a valve controller for preventing the forward movement of said elastic valve provided at the portion where the front periphery of said elastic valve is located in said outer needle body; and a backward movement controller for controlling the backward movement of said valve holding plate provided at the portion opposite to the rear periphery of said valve holding plate in said outer needle body.

4. The indwelling needle according to claim 1, wherein said elastic member is formed by a spring and a predetermined portion of said connector part is formed by a spring receiving portion projected from said outer peripheral surface of said connector part, said indwelling needle including a connector controller for controlling the backward movement of said connector part provided at the portion opposite to the rear end portion of said spring receiving portion in said outer needle body, whereby the tip end portion of said connector part is located within said insertion hole of said valve holding plate or near thereof as said spring receiving portion is contacted with said connector controller and the tip end portion of said connector part is passed through the opening and closing aperture of said elastic valve to project the rear surface side of said elastic valve when said connector part is forwardly moved against the elasticity of the spring.

5. The indwelling needle according to claim 1, wherein the inner peripheral surface of said insertion hole of said valve holding plate is formed into a tapered shape in which the diameter of the rear side portion is greater than that of the front side portion.

* * * * *